(12) United States Patent
Cardoso

(10) Patent No.: US 6,417,352 B1
(45) Date of Patent: Jul. 9, 2002

(54) PROCESS FOR THE ISOLATION OF A PHARMACEUTICALLY ACCEPTABLE ALKALI METAL SALT OF CLAVULANIC ACID

(75) Inventor: Joaquim P. Cardoso, Castanheira do Ribatejo (PT)

(73) Assignee: CIPAN-Companhia Industrial Produtora de Antibioticos, S.A., Castanheira do Ribatejo (PT)

( * ) Notice: Subject to any disclaimer, the term of this patent is extended or adjusted under 35 U.S.C. 154(b) by 0 days.

(21) Appl. No.: 09/381,884

(22) PCT Filed: Mar. 20, 1998

(86) PCT No.: PCT/EP98/01637

§ 371 (c)(1),
(2), (4) Date: Feb. 10, 2000

(87) PCT Pub. No.: WO98/42858

PCT Pub. Date: Oct. 1, 1998

(51) Int. Cl.$^7$ .................. C07D 503/18; C12P 17/18
(52) U.S. Cl. ........................................ 540/349
(58) Field of Search .......................... 540/349

(56) References Cited

U.S. PATENT DOCUMENTS 3,770,590 A  * 11/1973 Inamine ................ 195/80
4,490,294 A  * 12/1984 Fleming ................ 260/245.3
5,498,788 A     3/1996 Zmitek et al. ........... 540/349

FOREIGN PATENT DOCUMENTS

| | | |
|---|---|---|
| GB | WO/95/21173 A | 8/1995 |
| WO | WO/95/23870 | 9/1995 |
| WO | WO/96/28452 | 9/1996 |
| WO | WO/97/05142 | 2/1997 |

* cited by examiner

*Primary Examiner*—Mark L. Berch
(74) *Attorney, Agent, or Firm*—Kilpatrick Stockton LLP

(57) ABSTRACT

The invention relates to the process for the isolation of a pharmaceutically acceptable alkali metal salt of clavulanic acid from a fermentation broth containing impure clavulanic acid comprising the steps of filtration of the fermented broth, extraction of the clavulanic acid to a water immiscible or partly water immiscible solvent at pH from 1.2–2, precipitation of an alkali metal salt A of clavulanic acid by addition of a solution of an alkali metal alkylalkanoate, characterized by the following steps:

before the filtration the fermented broth containing clavulanic acid is diluted with water, a flocculating agent is added and the pH is adjusted to 3–5 for further purification the alkali metal salt A of clavulanic acid is converted to clavulanic acid by addition of an inorganic acid and is extracted into a water immiscible or partly water immiscible solvent a solution of a different alkali metal B alkyl alkanoate is added and the alkali metal salt B of clavulanic acid is precipitated.

23 Claims, No Drawings

PROCESS FOR THE ISOLATION OF A PHARMACEUTICALLY ACCEPTABLE ALKALI METAL SALT OF CLAVULANIC ACID

This application is filed under U.S.C. §371 from PCT/EP98/01637.

The present invention relates to a novel process for the isolation of the pharmaceutically acceptable alkali metal salt of clavulanic acid from a fermentation broth containing impure clavulanic acid comprising the steps of filtration of the fermented broth, extraction of clavulanic acid to a water immiscible or partly water immiscible solvent at a pH from 1.2 to 2, precipitation of the alkali metal salt A of clavulanic acid by addition of a solution of an alkali metal alkylalkanoate.

Clavulanic acid and its alkali metal salts and esters are used in pharmaceutical preparation to prevent the deactivation of β-lactam antibiotics. Commercial preparations of clavulanic acid contain potassium clavulanate in combination with amoxycillin trihydrate. Clavulanic acid is an unstable hygroscopic oil. Potassium clavulanate is more stable than the free acid or other salts, and is therefore most frequently, used for commercial preparations.

Clavulanic acid and its derivatives are inhibitors of the β-lactamases. The resistance of β-lactam antibiotics is associated with inactivation of β-lactam structure due to the opening of β-lactam ring by β-lactamase produced by bacteria. Thus the inactivating enzymes are commonly called as β-lactamase, they are divided into penicillinase and cephalosporinase.

Furthermore clavulanic acid itself is believed to have an antibacterial activity.

Clavulanic acid is produced from various strains of microorganism by a fermentation process. For this process for example strains belonging to the genus Streptomyces such as *S. clavuligerus* NRRL 3585 (U.S. Pat. No. 4,110,165), *S. jumonjinensis* NRRL 5741 (British Patent 1,563,103), *S. katsurahamanus* IFO 13716 (Japanese Patent 83,009,579), and Streptomyces sp. P6621 FERM 2804 (Japanese Patent 55,162,993) are used. For the preparation of clavulanic acid by a fermentation process the microorganism *Streptomyces clavuligerus* is preferred.

In the state of art different processes for the preparation and purification of the clavulanic acid containing fermentation broth are described.

GB 1 508 977 discloses preparation of clavulanic acid and its salts by filtration of the fermentation broth by passage through an anionic exchange resin.

GB 1 543 563 discloses a fermentation process wherein the pH value of the medium is maintained in the range of 6.3 to 6.7. A pharmaceutically acceptable salt such as potassium clavulanate is prepared by ion exchange process from lithium clavulanate. However lithium clavulanate is not a pharmaceutically acceptable salt. Therefore it is necessary to add an ion exchange process as a further step for preparing a pharmaceutically acceptable form of the compound. Furthermore, the remaining salt lithium chloride is soluble in organic solvents and therefore it is difficult to separate the lithium chloride in the aqueous phase during the extraction process.

Further documents of the state of the art like EP-0 647 229 describe the use of amine salts of clavulanic acid as intermediate compounds for the preparation and purification of clavulanic acid and its alkali metal salts. EP-0 647 229 for example describes a process for the preparation of a purified clavulanic acid or a salt or ester thereof by preparing a diamine salt of clavulanic acid and converting this intermediate compound into clavulanic acid or a pharmaceutically acceptable salt or ester. The conversion is made by adding for example potassium 2-ethylhexanoate and precipitating potassium clavulanate. Many of such amines are either unsuitable for the production of a salt of clavulanic acid or they give rise to amine salts of clavulanic acid which are either hygroscopic or toxic or both and, therefore, are unsuitable for use as intermediates for the preparation of a pharmaceutically acceptable compound.

Other purification processes of the state of the arts are performed without any amine compounds. For example WO 95/34194 A2 describes a process for manufacturing an alkali metal salt of clavulanic acid wherein impure clavulanic acid in aqueous solution is extracted by a solvent mixture of ketone and alkyl acetate under acidic condition. The solution is than treated in a conventional manner and the solution of an alkali metal salt of alkanoic acid dissolved in ketone or alkanol solvent is added to obtain pure alkali metal salt of clavulanic acid. Thus the process according to this state of the art omits the step of formation of amine salts. This process has the advantage that the use of mostly toxic amines is no longer necessary. In a preferred embodiment as alkali metal salt of alkanoic acid sodium or potassium salts are used, especially potassium 2-ethylhexanoate.

A similar process is also described in WO 96/28452 A1. This process comprises the steps of removing solids from a clavulanic acid containing fermentation broth by microfiltration, acidifying the filtrate to a pH between 1 and 3, extracting the acidified filtrate with a water immiscible solvent and separating the clavulanic acid containing extract. This extract is mixed with a metal donor and at least one additional solvent. From the solution the metal clavulanate salt is separated.

As metal donor compounds organic salts, carbonates, bicarbonates or hydroxides of potassium, sodium, lithium or magnesium can be used. The use of carboxylic acid salt is preferred. Further preferred metal donors include potassium 2-ethylhexanoate, potassium acetate, lithium 2-ethylhexanoate and lithium acetate.

EP-0 182 522 B1 also describes a process for the preparation of clavulanic acid and its salts and esters. In this process the fermentation broth is worked up as follows. The solids are removed by filtration or centrifugation. The broth is acidified to a pH of 1 to 3 and clavulanic acid is extracted by adding a water immiscible solvent with two phases being separated for example by centrifugation. This gives the clavulanic acid in the water immiscible phase. The solution is purified by mixing it with the dissolved lithium 2-ethylhexanoate solution isolating lithium clavulanate and optionally converting the lithium salt to other salts or an ester. The conversion of the lithium salt to other salts is carried out by ion exchange procedures using ion exchange resins in the form of the desired cation preferably sodium or potassium.

The processes of the state of the art referred above have the disadvantage, that the alkali metal salts prepared by direct precipitation are not pure enough for a pharmaceutical use. Therefore, further purification steps like recrystallization, purification over a column etc. are necessary.

The object of the invention therefore is to prepare clavulanic acid and its pharmaceutically acceptable alkali metal salts such as potassium clavulanate in a new and simple manner wherein the desired substance is obtained in a very high yield without any additional purification steps and of high purity avoiding the use of toxic amines or lithium compounds.

This technical problem is solved by a process which is characterized by the following steps:

before the filtration of the fermentation broth, the fermentation broth containing clavulanic acid is diluted with water, a flocculating agent is added and the pH is adjusted to pH 3 to 5, for further purification the alkali metal salt A of clavulanic acid is converted to clavulanic acid by addition of an inorganic acid and is extracted into a water immiscible or partly water immiscible solvent, and to the solution of clavulanic acid a solution of a different alkali metal alkylalkanoate B is added and the alkali metal salt B of clavulanic acid is precipitated.

Suitable salts according to the present invention are pharmaceutically acceptable alkali metal salts and alkaline earth metal salts like sodium, potassium, calcium and magnesium salts.

Of these compounds potassium clavulanate is the most stable compound which is normally used for pharmaceutical preparations. The clavulanic acid itself is an unstable hygroscopic oil which is not used for the preparation of pharmaceutical compounds.

In a preferred embodiment the alkylalkanoate is an alkylhexanoate, especially 2-ethylhexanoate. The alkali metal A is sodium and the alkali metal B is potassium.

In a further preferred embodiment the filtered broth containing clavulanic acid is purified after the filtration step by adsorption on an anion exchange resin containing column and eluted with an aqueous solution of an alkali metal salt. As anionic exchange resin for example DIAION® SA-11A is used. After the elution step clavulanic acid is extracted into a water immiscible solvent or a partly water immiscible solvent and sodium clavulanate is precipitated by the addition of sodium 2-ethylhexanoate solution in an appropriate solvent after dehydration with anhydrous sodium or magnesium sulphates and purification with activated carbon.

As an alternative process step it is also possible to carry out the direct extraction of the clavulanic acid contained in the filtered broth to a water immiscible or partly water immiscible solvent at an adequate pH between 1.2–2.0 without using a column. Preferably 3 to 4 volumes of solvent in relation to the filtered broth are used in this step. The clavulanic acid is extracted from the above solvent to an aqueous solution using an organic base, preferably triethylamine or diethylamine. In this operation, a concentration of about 10 to 15 times is obtained. The exhaust solvent can be re-used in the process without a purification step. The clavulanic acid is back extracted to a water immiscible or partly water immiscible solvent. From the solvent sodium clavulanate is precipitated by addition of the sodium 2-ethylhexanoate solution in an appropriate solvent after dehydration.

Clavulanic acid is a hygroscopic oil and is not very stable in aqueous solution. Therefore, this solution of clavulanic acid in a water immiscible or partly water immiscible solvent is dehydrated in a preferred manner by addition of anhydrous sodium or magnesium sulphate and further purified by addition of activated carbon. By the use of the activated carbon the coloured impurities are removed from the solution.

In a preferred embodiment as solvent ethyl acetate, butyl acetate, methyl isobutyl ketone or mixtures thereof are used. Furthermore, before the filtration step a flocculating agent can be used. As flocculating agents quaternary ammonium salts are preferred.

A further object of the present invention is the use of sodium clavulanate as intermediate compound for the preparation of the pharmaceutically acceptable potassium clavulanate.

Filtration of clavulanic acid fermented broth is normally difficult and the use of flocculating agents has been suggested to improve filterability of the whole broth as for example described in EP-A 0 387 178. The present invention describes a new simple and cheap method to improve not only the filterability of the whole broth but also a means of increasing the yield of filtration and a facilitation of the subsequent down stream process.

Surprisingly it has been found possible to improve the recovery of clavulanic acid from an aqueous fermented broth by pre-diluting it with water. This pre-dilution of the fermented broth when combined with the use of flocculating agents and pH-adjustment is even more efficient, both at the level of filterability and yield of filtration and subsequent down stream operations. The pre-dilution of the broth with water decreases the viscosity of the same making the filtration easier. The yield of filtration is also improved since a poorer filtrate remains in the filter cake. The use of a flocculating agent and the gentle acidification to a pH value of 3 to 5 leads to precipitation of proteins which will be retained in the filter cake improving the filtration rate. In this way, a purer filtrate is obtained implying that the further recovery operations for the clavulanic acid are much easier. According to the present invention high quality potassium clavulanate can be produced with good yields from the fermented broth of clavulanic acid producing microorganisms through the steps which are described in the characterizing part of claim 1.

After filtration of the fermented broth the solution can be directly extracted to an organic solvent at an adequate pH is about 1.2 to 2.0, preferably using 3 to 4 volumes of solvent in relation to the filtered broth. It is also possible to adsorb the solution before that step onto an anionic exchange resin and to elute clavulanic acid with an aqueous solution of an alkaline metal salt. The extraction step leads to an organic phase which contains the clavulanic acid from the fermentation process. The organic phase is dehydrated with anhydrous sodium or magnesium sulphate and purified with activated carbon. Thereafter sodium 2-ethylhexanoate in an organic solution is added and after a period of crystallization crystals of sodium clavulanate can be collected by filtration.

The conversion from sodium clavulanate to potassium clavulanate is carried out by extraction of clavulanic acid to an adequate solvent and crystallization of potassium clavulanate after dilution of the acid with an adequate solvent and addition of potassium 2-ethylhexanoate or potassium acetate solution in an appropriate solvent. For this process step sodium clavulanate is suspended in a mixture of methyl isobutyl ketone or ethyl acetate or butyl acetate with water. To this solution an inorganic acid is added. By this addition the salt of the clavulanic acid is converted into clavulanic acid. The acid is extracted into the organic phase with stirring.

The mixture is then diluted with isopropanol and a solution of potassium 2-ethylhexanoate in isopropanol is added to reach a pH between 6 and 7. After a crystallization period of 2 hours at low temperature potassium clavulanate crystals can be collected by filtration.

If necessary potassium clavulanate can be recrystallized.

In a further preferred embodiment it is possible to extract the clavulanic acid from the water immiscible or partly water immiscible solvent to an aqueous solution using an organic phase preferably triethylamine or diethylamine. By this operation concentration of about 10 to 15 times can be obtained. The exhaust solvent can be reused in the process without any purification step.

A further alternative way is a back extraction of clavulanic acid to the water immiscible or partly immiscible solvent.

By the process of the present invention clavulanic acid salts of potassium can be prepared in high purity and good yields. The process is simple and allows to work without the use of any toxic amines. Furthermore the purity of the potassium clavulanic acid prepared by the present invention is higher then the purity of this compound made from processes of the state of the art which directly use the precipitation by reaction with potassium 2-ethylhexanoate.

The following examples are intended to illustrate the present not to limit it.

A. Experiments of Filtration of Fermented Broth of Clavulanic Acid

EXAMPLE 1

Effect of Pre-dilution of Fermented Both with Water on the Rate and Yield of Filtration Portions of 200 ml of clavulanic acid fermented broth, to which 4% (w/v) of filter aid (Dicalite 478) was added, were water and filtered under vacuum in a Buckner filter.

The rates and yields of filtration obtained are shown in Table 1

TABLE 1

| Percentage of pre-dilution with water (v/v) | Filtration rate ($1\ m^{-2}h^{-1}$) | Yield of filtration (%) |
| --- | --- | --- |
| 0 | 16 | 85.3 |
| 10 | 18 | 87.5 |
| 20 | 20 | 90.1 |
| 30 | 25 | 91.6 |
| 40 | 30 | 92.5 |
| 50 | 35 | 92.6 |
| 60 | 30 | 92.8 |
| 70 | 28 | 93.5 |

EXAMPLE 2

Combined Effect of Fermented Broth Pre-dilution and Use of Flocculating Agents on the Rate and Yield of Filtration Portions of 200 ml of clavulanic acid fermented broth were treated 4 % (w/v) of filter aid (Dicalite 478) and with 0.4% (v/v) of Rolquat CDM-BC as flocculating agent. Each of the 200 ml portion was diluted with water and filtered as described in example 1.

The rates of filtration obtained were as shown in Table 2. The yields of filtration were similar to those obtained in Example 1.

TABLE 2

| Percentage of pre-dilution with water (v/v) | Filtration rate ($1\ m^{-2}h^{-1}$) |
| --- | --- |
| 0 | 25 |
| 10 | 30 |
| 20 | 35 |
| 30 | 42 |
| 40 | 46 |
| 50 | 50 |
| 60 | 45 |
| 70 | 40 |

EXAMPLE 3

Combined Effect to Fermented Broth Pre-dilution with the Use of a Flocculating Agent and pH Adjustment to 4.5 on the Rate and Yield of Filtration Portions of 200 ml of clavulanic acid fermented broth were treated with 4% (w/v) of filter aid (Dicalite 478) and with 0.4% (v/v) of the flocculating agent used in Example 2. Then, the pH of each of these 200 ml portions of fermented broth was adjusted to pH 4.5 with 15 % (w/v) sulphuric acid. Each portion was diluted with water and filtered as in Example 1. The rates of filtration obtained are shown in Table 3. The yields of filtration obtained were similar to those obtained in Example 1.

TABLE 3

| Percentage of pre-dilution with water (v/v) | Filtration rate ($1\ m^{-2}h^{-1}$) |
| --- | --- |
| 0 | 50 |
| 10 | 55 |
| 20 | 60 |
| 30 | 62 |
| 40 | 70 |
| 50 | 75 |
| 60 | 70 |
| 70 | 65 |

B. Preparation of the Intermediate Salt of Clavulanic Acid

The following examples illustrate the preparation of the intermediate salt of clavulanic acid (sodium clavulanate).

EXAMPLE 4

750 l of fermented broth of *Streptomyces clavuligerus*, assaying about 3800 µg/ml (as clavulanic acid), were treated with 4% (w/v) of filter aid, prediluted with 40 % of deionised water and filtered in a press filter after the addition of 0.4% (v/v) of a flocculating agent (Rolquat CDM BC) and after the adjustment of the pH to 4.5 with 15% sulphuric acid (w/v). After the filtration, the cake was washed with 10% (v/v) of water leading to a total volume of filtered broth of about 1100 l, with an assay of 2500 µg/ml (yield of filtration about 92%).

The filtrate containing the clavulanic acid was adsorbed onto an anionic resin (Diaion SA-11A) in columns and the adsorbed clavulanic acid eluted with a solution of a 1.0M sodium chloride. The combined yield of adsorption/elution was approximately 85% of the theoretical and the average concentration of the mixed rich eluate obtained was about 10000 µg/ml. This eluate was extracted with 4 volumes of ethyl acetate at pH around 1.4 with 25% (w/v) sulphuric acid to give an ethyl acetate extract with a concentration of about 2000 µg/ml. Butyl acetate or methyl isobutyl ketone can also be used. The ethyl acetate extract was treated with anhydrous sodium sulphate and activated carbon and filtered using a Buckner type filter. The filtrate obtained was again treated with anhydrous sodium sulphate and filtered.

From the dehydrated, purified ethyl acetate extract the intermediate sodium clavulanate was obtained as follows:

A 0.3 M solution of sodium 2-ethylhexanoate in ethyl acetate was prepared. This solution was treated with anhydrous sodium sulphate and activated carbon and filtered. Afterwards, this clear solution was added to the ethyl acetate extract, for one hour, to reach a pH within the range 6.0–6.2. After this addition, and after a period of crystallization, of approximately one hour at low temperature (5° C.), the crystals of sodium clavulanate were collected by filtration (centrifugation can also be used) washed two times with acetone and dried with a stream of nitrogen gas under vacuum. The analysis of the sodium clavulanate was 70% (as clavulanic acid) meaning a global yield from the whole broth of about 58% of the theoretical.

EXAMPLE 5

The intermediate salt was prepared as in Example 1 with the following differences:

The solvent used to extract clavulanic acid from the mixed rich eluate was butyl acetate which was dehydrated with anhydrous sodium sulphate and purified with activated carbon. After solids removal, purified butyl acetate was treated with a 0.3 M solution of sodium 2-ethylhexanoate in ethyl acetate. The crystallization of the sodium clavulanate was effected during 1.5 hours at 5° C. The analysis of the sodium clavulanate was about 70% as clavulanic acid and the yield from the whole broth about 45% of the theoretical.

EXAMPLE 6

The intermediate salt was obtained as in Example 1 with the following differences:

The solvent used to extract clavulanic acid from the rich eluate was methyl isobutyl ketone which after extraction was dehydrated with anhydrous sodium sulphate and purified with activated carbon. After solids removal, the purified methyl isobutyl ketone containing clavulanic acid was treated with a solution of a 0.3M sodium 2-ethylhexanoate in methyl isobutyl ketone. The crystallization of sodium clavulanate was effected during 1.5 hours at 5° C. The analysis of the sodium clavulanate was about 70% as clavulanic acid and the final yield from the whole broth about 50% of the theoretical.

EXAMPLE 7

The intermediate salt was obtained as in Example 1 with the following differences:

Filtered broth was extracted directly to ethyl acetate. Afterwards clavulanic acid was extracted to an aqueous solution using triethylamine. Clavulanic acid in the aqueous solution was back extracted to the same solvent and the crystallization on of sodium clavulanate was performed using a 0.3 M solution of sodium 2-ethylhexanoate in ethyl acetate.

The analysis of the sodium clavulanate obtained was 72% (as clavulanic acid) and the global yield obtained from the whole broth was approximately 50% of the theoretical.

C. Preparation of Pure Potassium Clavulanate

EXAMPLE 8

1.5 kg (as clavulanic acid) of intermediate sodium clavulanate, prepared according to the procedures described in part B Examples 4 to 7, were suspended in a mixture of methyl isobutyl ketone and deionised water (97/3, v/v) at a temperature of 5° C. Diluted pure hydrochloric acid was added to reach pH 1.3 and the clavulanic acid was extracted to the organic phase with stirring. After phase separation by gravity, the rich methyl isobutyl ketone was dehydrated with anhydrous sodium sulphate (80 g/l) at low temperature. The sodium sulphate was removed by filtration and the filtrate obtained was treated again with more anhydrous sodium sulphate (20 g/l) and decolourized with activated carbon. After filtration, using diatomite as filter aid, the rich solvent obtained was diluted with isopropanol.

To the mixture thus obtained, a 0.3M solution of potassium 2-ethylhexanoate in isopropanol was added for 1.5 hours, to reach a pH around 6.5. After the addition of the potassium 2-ethylhexanoate solution and a crystallization period of 2 hours at low temperature, the potassium clavulanate crystals were collected by filtration in a closed filter, washed with acetone, pressed with a nitrogen stream and dried under vacuum at room temperature to a moisture level below 0.5%. The assay of the product obtained was 82% (as clavulanic acid). The conversion yield from sodium clavulanate was 80% of the theoretical.

EXAMPLE 9

1.5 kg (as clavulanic acid) of intermediate sodium clavulanate were suspended in a mixture of butanol/water (90/10, v/v) and diluted pure hydrochloric acid was added until pH 1.3, keeping the temperature below 5° C. The sodium salt of clavulanic acid was converted into clavulanic acid and extracted to the solvent. The aqueous phase was separated by gravity. After phase separation, the water in the solvent was removed by azeotropic distillation at reduced pressure, and the rich concentrated solvent was treated with activated carbon and filtered. To the rich purified filtered solvent, a 0.3M solution of potassium 2-ethylhexanoate in butanol was added for 1.5 hours, at room temperature.

After the addition of the potassium 2-ethylhexanoate solution, the reaction mixture was cooled to 5° C. and after a crystallization period of 1.5 hours, the potassium clavulanate crystals were collected by filtration in a closed filter, washed with acetone, pressed with a nitrogen stream, and dried under vacuum at room temperature to a moisture level below 0.5%.

The assay of the product obtained was 81% (as clavulanic acid). The conversion yield from sodium clavulanate was 75% of the theoretical.

EXAMPLE 10

1.5 kg (as clavulanic acid) of intermediate sodium clavulanate prepared according to the procedures of part B examples 4 to 7, were suspended in a mixture of butyl acetate/water (97/3, v/v) and diluted pure hydrochloric acid was added until pH 1.3. The temperature was kept below 5° C. The sodium salt of clavulanic acid was converted into clavulanic acid and extracted to the solvent. After extraction and phase separation, the rich butyl acetate phase was treated with anhydrous sodium sulphate and activated carbon, and filtered. The rich filtered solvent obtained was diluted with isopropanol. To the mixed solvent obtained, a 0.3M solution of potassium 2-ethylhexanoate in isopropanol was added for 1.5 hours, to reach a pH around 6.5. After a crystallization period of 2 hours, at 5° C., the crystals of potassium clavulanate were recovered by filtration in a closed filter, washed with acetone, pressed with a nitrogen stream, and dried under vacuum at room temperature to a moisture level lower than 0.5%. The conversion yield from sodium clavulanate was 78% of the theoretical.

EXAMPLE 11

Recrystallization of Potassium Clavulanate

When required potassium clavulanate can be purified as described in the example below. A mixture of methyl isobutyl ketone and water (98/2, v/v), was prepared. Potassium clavulanate was suspended in the previously prepared mixture, and diluted pure hydrochloric acid was added until pH 1.3. The temperature was kept below 5° C. The potassium clavulanate was converted into clavulanic acid and extraced to the solvent. After extraction and phase separation, the rich methyl isobutyl ketone was treated with anhydrous sodium sulphate and activated carbon, and filtered. Isopropanol was added to the methyl isobutyl ketone and a 0.3M solution of potassium 2-ethylhexanoate in isopropanol was added for 1 hour at room temperature. After a crystallization period of 3 hours at 5° C., the crystals of potassium clavulanate were recovered by filtration in a closed filter, washed with anhydrous acetone, pressed with a nitrogen stream and dried under vacuum at room temperature, to reach a moisture level lower than 0.5%. The yield of recrystallization was about 80% of the theoretical.

What is claimed is:

1. A method for isolating a pharmaceutically acceptable alkali metal salt of clavulanic acid from a fermentation broth comprising clavulanic acid, comprising:

a) diluting a fermentation broth comprising clavulanic acid by adding water in a volume equal to between ten percent and seventy percent of the volume of the fermentation broth, resulting in a diluted fermentation broth comprising clavulanic acid;

b) filtering the diluted fermentation broth of a), resulting in a filtered fermentation broth comprising clavulanic acid;

c) extracting the clavulanic acid to a water immiscible or partly water immiscible solvent, resulting in a solution comprising clavulanic acid;

d) adding a solution of a first alkali metal alkylalkanoate to the solution of c), and precipitating an alkali metal salt A of clavulanic acid;

e) converting the alkali metal salt A of clavulanic acid to clavulanic acid by adding an inorganic acid;

f) extracting the clavulanic acid to a water immiscible or partly water immiscible solvent; and g) adding a second alkali metal alkylalkanoate and precipitating an alkali metal salt B of clavulanic acid.

2. The method of claim 1, wherein the alkali metal A is sodium and the alkali metal B is potassium.

3. The method of claim 1, wherein, prior to extracting the clavulanic acid to a water immiscible or partly water immiscible solvent, c) further comprises:

i) adsorbing the clavulanic acid of b) on an anion exchange resin containing column, and ii) eluting the clavulanic acid adsorbed onto the anion exchange resin containing column with an aqueous solution comprising an alkali metal salt, resulting in an eluate comprising an alkali metal salt of clavulanic acid;

wherein the extraction in c) comprises adjusting the pH of the eluate to a value effective to convert the alkali metal salt of clavulanic acid in ii) to clavulanic acid and combining the eluate with the water immiscible or partly water immiscible solvent.

4. The method of claim 1, wherein c) further comprises dehydrating the water immiscible or partly water immiscible solvent containing the clavulanic acid.

5. The method of claim 4, wherein dehydrating comprises adding anhydrous sodium sulfate or anhydrous magnesium sulfate to the solvent.

6. The method of claim 1, wherein c) further comprises adding activated carbon to the water immiscible or partly water immiscible solvent containing the clavulanic acid.

7. The method of claim 1, wherein, after extracting the clavulanic acid to the water immiscible or partly water immiscible solvent in c), c) further comprises:

i) combining the solution comprising clavulanic acid in c) with an aqueous solution and an organic base under conditions effective to cause extraction of a salt of clavulanic acid to the aqueous solution, and ii) combining the aqueous solution of i) with a water immiscible or partly water immiscible solvent under conditions effective to cause extraction of clavulanic acid to the aqueous solution;

wherein the volume of water immiscible or partly water immiscible solvent in c) is between three and four times the volume of the filtered fermentation broth.

8. The method of claim 1, wherein the water immiscible or partly water immiscible solvents each are selected from the group consisting of ethyl acetate, butyl acetate, methyl isobutyl ketone, or any combination thereof.

9. The method of claim 1, wherein, after diluting the fermentation broth, a) further comprises combining a flocculating agent with the diluted fermentation broth.

10. The method of claim 9, wherein, after diluting the fermentation broth and prior to combining a flocculating agent with the diluted fermentation broth, a) further comprises adjusting the pH of the fermentation broth to between 3 and 5.

11. The method of claim 9, wherein the flocculating agent comprises a quaternary ammonium salt.

12. The method of claim 10, wherein the flocculating agent comprises a quaternary ammonium salt.

13. The method of claim 1, wherein, after extracting the clavulanic acid to the water immiscible or partly water immiscible solvent in c), c) further comprises:

i) combining the solution comprising clavulanic acid in c) with an aqueous solution and an organic base under conditions effective to cause extraction of a salt of clavulanic acid to the aqueous solution, and ii) combining the aqueous solution of i) with a water immiscible or partly water immiscible solvent under conditions effective to cause extraction of clavulanic acid to the water immiscible or partly water immiscible solvent.

14. The method of claim 1, wherein the alkylalkanoate in d) is an alkylhexanoate.

15. The method of claim 1, wherein the alkylalkanoate in d) is 2-ethylhexanoate.

16. The method of claim 1, wherein the volume of water added to the fermentation broth in a) is between about forty percent and about sixty percent of the volume of the fermentation broth.

17. The method of claim 1, wherein the alkylalkanoate in g) is an alkylhexanoate.

18. The method of claim 1, wherein the alkylalkanoate in g) is 2-ethylhexanoate.

19. The method of claim 13, wherein the organic base is triethylamine or diethylamine.

20. The method of claim 1, wherein f) further comprises dehydrating the water immiscible or partly water immiscible solvent containing the clavulanic acid.

21. The method of claim 20, wherein dehydrating comprises adding anhydrous sodium sulfate or anhydrous magnesium sulfate to the solvent.

22. The method of claim 1, wherein f) further comprises adding activated carbon to the water immiscible or partly water immiscible solvent containing the clavulanic acid of f) prior to adding a solution of a second alkali metal alkylalkanoate to the solvent of f).

23. The method of claim 7, wherein the organic base is triethylamine or diethylamine.

* * * * *